(12) United States Patent
Joabsson et al.

(10) Patent No.: US 8,865,021 B2
(45) Date of Patent: Oct. 21, 2014

(54) COMPOSITIONS OF LIPIDS AND CATIONIC PEPTIDES

(75) Inventors: Fredrik Joabsson, Lund (SE); Fredrik Tiberg, Lund (CH)

(73) Assignee: Camurus AB, Lund (SE)

(*) Notice: Subject to any disclaimer, the term of this patent is extended or adjusted under 35 U.S.C. 154(b) by 1302 days.

(21) Appl. No.: 10/578,609

(22) PCT Filed: Nov. 5, 2004

(86) PCT No.: PCT/GB2004/004696
§ 371 (c)(1),
(2), (4) Date: Nov. 3, 2006

(87) PCT Pub. No.: WO2005/046642
PCT Pub. Date: May 26, 2005

(65) Prior Publication Data
US 2007/0080323 A1 Apr. 12, 2007

(30) Foreign Application Priority Data

Nov. 7, 2003 (GB) .................................... 0326074.2
Nov. 7, 2003 (GB) .................................... 0326075.9
Jun. 4, 2004 (GB) .................................... 0412544.9

(51) Int. Cl.
*C09K 19/00* (2006.01)
*A61K 9/66* (2006.01)
*B01J 13/00* (2006.01)
*A61K 38/11* (2006.01)
*A61K 38/31* (2006.01)
*A61K 38/23* (2006.01)
*A61K 9/127* (2006.01)

(52) U.S. Cl.
CPC .................. *A61K 38/11* (2013.01); *A61K 38/31* (2013.01); *A61K 38/23* (2013.01); *A61K 9/1274* (2013.01); *Y10S 514/937* (2013.01); *Y10S 514/964* (2013.01)
USPC ...... 252/299.01; 424/450; 424/455; 424/458; 424/459; 428/357; 428/402; 514/937; 514/964

(58) Field of Classification Search
USPC ............. 252/299.01, 302; 428/302, 402, 357; 424/450, 455, 458, 459; 514/937, 964
See application file for complete search history.

(56) References Cited

U.S. PATENT DOCUMENTS 5,531,925 A 7/1996 Landh et al.
6,770,466 B2* 8/2004 Shi et al. ...................... 435/194

FOREIGN PATENT DOCUMENTS

WO 95/34287 A 12/1995
WO 99/56725 A 11/1999
WO 2004/080438 A 9/2004

OTHER PUBLICATIONS

Rawlings, Neil; Biochem. J. (2004) 378, 705-716.*

(Continued)

*Primary Examiner* — Vasu Jagannathan
*Assistant Examiner* — Preeti Kumar
(74) *Attorney, Agent, or Firm* — Nixon & Vanderhye P.C.

(57) ABSTRACT

The present invention relates to compositions containing at least one cationic peptide active agent, at least one neutral structure forming amphiphile, at least one anionic structure forming amphiphile and optionally at least one solvent wherein the composition is in the form of a non-lamellar phase structure and/or forms a nonlamellar phase structure on exposure to body fluids. The invention also relates to methods for protecting peptides from enzymic degradation in vivo and to compositions in which the peptide active agent is so protected.

19 Claims, 3 Drawing Sheets

(56) References Cited

OTHER PUBLICATIONS

Lee et al., "Combined effect of oleic acid and polyethylene glycol 200 on buccal permeation of (D-Ala2, D-Leu5)enkephalin from a cubic phase of glyceryl monooleate", International Journal of Pharmaceutics, vol. 204, No. 1-2, Aug. 25, 2000, pp. 137-144, XP002320191.

Ericsson et al., "Cubic Phases as Delivery Systems for Peptide Drugs", Polymeric Drugs and Drug Delivery Systems ACS Symposium Series, vol. 469, 1991, pp. 251-265, XP009044713.

Shah Jaymin et al., "Cubic phase gels as drug delivery systems", Advanced Drug Delivery Reviews, vol. 47, No. 2-3, Apr. 25, 2001, pp. 229-250, XP002320651.

Chang et al., "Effect of dissolution media and additives on the drug release from cubic phase delivery systems", Journal of Controlled Release, vol. 46, No. 3, Jun. 2, 1997, pp. 215-222, XP004092167.

Siekmann et al., "Preparation and structural investigations of colloidal dispersions prepared from cubic monoglyceride-water phases", International Journal of Pharmaceutics, vol. 244, 2002, pp. 33-43, XP002981485.

\* cited by examiner

COMPOSITIONS OF LIPIDS AND CATIONIC PEPTIDES

This application is the US national phase of international application PCT/GB2004/004696, filed 5 Nov. 2004, which designated the U.S. and claims priority of GB 0326075.9, filed 7 Nov. 2003; GB 0326074.2, filed 7 Nov. 2003; and GB 0412544.9, filed 4 Jun. 2004, the entire contents of each of which are hereby incorporated by reference.

The present invention relates to the protection, stabilisation and delivery of peptides and proteins in pharmaceutical and neutraceutical compositions. In particular, the invention relates to compositions and formulations for delivering cationic poly- and oligo-peptides in lipid based delivery systems so as to provide better protection against degradation by peptidases and proteases. The invention also relates to methods for formulating and delivering such peptides so as to provide such protection.

There is an enormous potential in the use of peptides and proteins for treating various disease states, as well as in prophylaxis and in improving general health and wellbeing of subjects. However, the performance of administered peptide agents is generally limited due to poor bioavailability, which in turn is caused by the rapid degradation of peptides and proteins in biological fluids. This increases the dose which must be administered and in many cases restricts the effective routes of administration. These effects are further exaggerated by the often limited permeability of peptides and proteins across biological membranes.

Peptides and proteins that are administered to the mammalian body (e.g. orally, intramuscularly etc.) are subject to degradation by various proteolytic enzymes and systems present throughout the body. Well known sites of peptidase activity include the stomach (e.g. pepsin), and the intestinal tract (e.g. trypsin, chymotrypsin, and others) but other peptidases (e.g. the carboxypeptidases A, B & C) are found throughout the body. Upon oral administration, gastric and intestinal degradation reduces the amount of peptide or protein which potentially could be absorbed through the intestinal surface lining and thereby decrease their bioavailability. Similarly, free peptides and proteins in the mammalian blood stream are also subject to enzymic degradation (e.g. by plasma carboxy peptidases etc.).

A small number of the proteases (peptidases) found in the mammalian body are indicated in Table 1, along with their type and common sites of action.

TABLE 1

| PROTEASE | SOURCE | TYPE |
| --- | --- | --- |
| Chymotrypsin A & B | Intestine | Serine protease |
| Chymotrypsin C | Intestine | Serine protease |
| Trypsin | Intestine | Serine protease |
| Elastase | Intestine | Serine protease |
| Pepsin A | Stomach | Aspartic protease |
| Carboxypeptidase A | Intestine | Zinc metallo protease |
| Carboxypeptidase B | Intestine | Zinc metallo protease |
| Carboxypeptidase C | Ubiquitous | Serine protease |
| Cathepsin B | Lysosomes | Cysteine protease |
| Cathepsin C | Ubiquitous | Cysteine protease |
| Cathepsin G | Polymorphonuclear leukocytes | Serine protease |
| Cathepsin H | Lysosomes | Cysteine protease |
| Cathepsin X | Ubiquitous | Cysteine protease |
| Aminopeptidase A | Ubiquitous, membrane bound | Zinc metallo protease |
| Aminopeptidase B | Ubiquitous, cytosolic or membrane bound | Zinc metallo protease |

Low permeability and absorption is another major obstacle leading to poor bioavailability of peptides in oral systems. Lipid carriers have is some cases been shown to significantly enhance the absorption of peptides and proteins but generally the (especially oral) bioavailability of peptide agents is so low as to render them essentially ineffective.

Two examples of cationic peptide active agents are the cyclic nonapeptide desmopressin, the 8-amino acid cyclic somatostatin analogue octreotide and the 32-amino acid peptide calcitonin.

Calcitonin is a naturally occurring peptide hormone secreted by the parafollicular cells of the mammalian thyroid gland and is also found in birds and fish. From all origins, calcitonin is a 32-residue peptide with one disulphide bridge and although some residues are conserved universally, some calcitonins vary significantly in other parts of their primary sequence. Calcitonin is produced naturally in response to elevated plasma calcium levels and can be used in the control, treatment and prophylaxis of conditions such as Paget's disease of bone, hypercalcemia and post-menopausal osteoporosis.

The most commonly administered calcitonins for human use are synthetic human calcitonin, and synthetic salmon calcitonin (which is around 50 times as potent by weight as the human hormone). Calcitonin can be administered only by parenteral routes due partly to rapid degradation in the gastrointestinal tract (GI tract). Usually, administration is intravenous (IV), intramuscular (IM) or subcutaneous (SC). This is necessary, but is undesirable because treatment with calcitonin is usually prolonged and a patient will typically have to self-administer the hormone by subcutaneous injection on a regular basis, often at alternating sites. As a result, an effective oral formulation would be a significant advance.

Desmopressin is a synthetic analogue of the natural human posterior pituitary hormone arginine vasopressin. Desmopressin is an antidiuretic and is used to prevent or control polydipsia, polyuria, and dehydration in patients with a deficiency in endogenous posterior pituitary vasopressin (e.g. in diabetes insipidus).

Unlike calcitonin, desmopressin may be administered orally due to high potency and limited side effects but its oral availability remains extremely low. Nasal or intravenous administration are considerably more effective than ingestion, with nasal administration giving at least 20 times the bioavailability of the oral formulation and intravenous administration being more than 600 times as effective. Nonetheless, oral administration of desmopressin is highly preferred and it would be of considerable advantage to provide oral compositions of this peptide with greater bioavailability.

Octreotide is a synthetic analogue of common regulatory hormone somatostatin (also known as growth hormone release inhibiting factor or somatotropin release inhibiting factor) which has effects not only through the control of the growth hormone somatotropin but also through altering secretion of some anterior pituitary hormones, pancreatic endocrine and exocrine function, gastric acid and GI hormone production and other mechanisms. Octreotide is available for intravenous, subcutaneous and long-term intra-muscular administration and thus a viable oral formulation would be of considerable value.

As illustrated in the above examples, there is a considerable need for a method by which peptide active agents may be protected from the proteolytic activity of the GI tract. There is also a need for a method by which peptides may be formulated for intramuscular or subcutaneous "depot" injection and remain protected from degradation within the body for longer periods of time.

The formulation of active agents with amphiphiles such as lipids has recently generated significant interest. Lipids have a polar, hydrophilic group and a non-polar hydrophobic group and these groups can assemble through mutual interactions into a variety or ordered and disordered structures in the presence of polar and/or non-polar solvents. Where the spontaneous curvature of the lipid is low, these structures are typically lamellar, such as mono- or multi-lamellar vesicles and liposomes and where the spontaneous curvature is higher, micellar phases or liquid crystalline phases dominate.

Amphiphile-based formulations show considerable potential in the delivery of many substances, especially for in vivo delivery to the human or animal body. Because the amphiphile has both polar and apolar groups which cluster to form polar and apolar regions, it can effectively solubilise both polar and apolar compounds. In addition, many of the structures formed by amphiphiles/structuring agents in polar and/or apolar solvents have a very considerable area of polar/apolar boundary at which other amphiphilic compounds can be adsorbed and stabilised. Amphiphiles can also be formulated to protect active agents, to at least some extent, from aggressive biological environments and thereby provide advantageous rates and sites of active agent release.

The formation of non-lamellar regions in the amphiphile/water, amphiphile/oil and amphiphile/oil/water phase diagrams is a well known phenomenon. Such phases include liquid crystalline phases such as the cubic P, cubic D, cubic G and hexagonal phases, which are fluid at the molecular level but show significant long-range order, and the $L_3$ phase which comprises a multiply interconnected bi-continuous network of bilayer sheets which are non-lamellar but lack the long-range order of the liquid crystalline phases. Depending upon their curvature, these phases may be described as normal (mean curvature towards the apolar region) or reversed (mean curvature towards the polar region).

The non-lamellar liquid crystalline and $L_3$ phases are thermodynamically stable systems. That is to say, they are not simply a meta-stable state that will separate and/or reform into layers, lamellar phases or the like, but are the stable thermodynamic form of the mixture.

Both lamellar and non-lamellar systems have been investigated for their properties as carriers and/or excipients for dietary, cosmetic, nutritional, diagnostic and pharmaceutical agents but the non-lamellar systems are thought to have considerable advantages in terms of their high internal surface area and bicontinuous polar and apolar regions. This has led to considerable investigation of non-lamellar phases particularly in controlled-release formulations and for solubilising relatively insoluble compounds.

As discussed above, the bulk non-lamellar phase is typically a thermodynamically stable system. In addition, this bulk phase may be dispersed in a polar or non-polar solvent to form particles of a non-lamellar (especially liquid crystalline) phase in a bulk solvent. This allows the advantages of bulk non-lamellar phases to be applied in situations where use of a bulk formulation that was not miscible with a body fluid would cause problems, such as in parenteral applications. Further control of a compound's release profile may also be achieved by, for example, optimising the size, morphology and drug-carrier membrane interactions of such dispersions.

In many cases, a liquid crystalline or $L_3$ phase is in or near thermodynamic equilibrium with the excess solvent and therefore stable dispersions of non-lamellar particles can be prepared. Such particles may be fully (i.e. thermodynamically) stable, or may gradually degrade, thereby providing control over the release profile for active agents formulated therewith. The formation of dispersions can be spontaneous or as the result of mechanical force introduced by, for example, shearing or ultrasound. These non-lamellar particles are of considerable interest in the delivery of active agents and have been proposed as carriers for many such actives.

A method for the formation of dispersed particles of non-lamellar phase in solvents such as water is described in U.S. Pat. No. 5,531,925. Such particles have a non-lamellar liquid crystalline or $L_3$ interior phase, or combinations thereof and typically a lamellar or $L_3$ surface phase.

Known particles of liquid crystalline or $L_3$ interior phase may be formed by methods such as adding to this phase a solution of surface-phase forming and stabilising agents, stirring to form a coarse dispersion and fragmenting the resulting mixture. Non-lamellar particles may also form spontaneously when dissolving a suitable composition of structure forming and fragmenting/stabilising agents in solvent.

In order to assess the presence of a liquid crystalline phase, the liquid crystalline order discussed above may be examined by use of small-angle X-ray diffraction (SAX), cryo-Transmission Electron Microscopy (cryo-TEM) or Nuclear Magnetic Resonance (NMR) spectroscopy studies. The sizes and size distributions of the dispersed particles may be examined by light scattering, particularly by use of laser light scattering or laser light diffraction instruments.

Emulsion, micellar or non-lamellar phase formulations are generally formed from mixtures containing at least one amphiphile with at least one hydrophilic "head" group and at least one hydrophobic "tail" group. In most naturally occurring lipids, these groups are joined by an ester linkage with the "tail" consisting of the hydrocarbon chain of the fatty acid(s). Typically, therefore, amphiphile-containing preparations of active agents contain either natural ester-containing lipids, synthetic (i.e. not found in natural extracts) amphiphiles or mixtures thereof.

The present inventors have now unexpectedly established that the lifetime of cationic peptides upon oral administration or subcutaneous or intramuscular injection may be considerably increased by formulation of the cationic peptides in a non-lamellar formulation wherein the formulation comprises an anionic amphiphile, particularly a fatty acid.

In a first aspect, the present invention therefore provides a composition comprising at least one cationic peptide active agent, at least one neutral structure forming amphiphile, at least one anionic structure forming amphiphile and optionally at least one solvent wherein said composition comprises a non-lamellar phase structure and/or forms a non-lamellar phase structure on exposure to body fluids. Preferably, the composition will be suitable for administration to a mammalian body such as a human, canine, feline, bovine, equine, porcine, caprine or ovine body, most preferably a human body. Furthermore, the non-lamellar phase structure adopted or formed by the composition will preferably be non-lamellar phase particles.

In a further aspect, the present invention also provides a method of medical treatment of a human or animal body comprising forming a composition of a peptide active agent sensitive to enzymatic degradation, at least one neutral structure forming amphiphile, at least one anionic structure forming amphiphile or salt thereof and optionally at least one solvent, and administering said composition to said subject, wherein said composition comprises particles of non-lamellar phase and/or forms particles of non-lamellar phase on exposure to body fluids. Preferably, the treatment method will be carried out on a mammalian body such as a human, canine, feline, bovine, equine, porcine, caprine or ovine body, most preferably a human body. Preferably, the administration will be intravenously, orally, intramuscularly, topically or subcutaneously.

The present invention results in a considerably higher oral bioavailability in mammalian subjects than has previously been achievable. In particular, this can be seen as a higher proportion of the administered dose being detectable in the bloodstream, relative to the amount that would be present if the same dose were administered directly (e.g. intravenously in saline solution).

In a further aspect, the invention therefore provides a composition comprising at least one cationic peptide active agent, at least one neutral structure forming amphiphile, at least one anionic structure forming amphiphile and optionally at least one solvent wherein said composition comprises non-lamellar phase (especially particles thereof) and/or forms non-lamellar phase (especially particles thereof) on exposure to body fluids and wherein the oral bioavailability of said active agent is at least 1% when measured as blood plasma concentration of active agent relative to intravenous administration in saline solution.

In a still further aspect, the invention similarly provides a method for oral delivery of at least 1% of a protease-sensitive (e.g. carboxpeptidase C-sensitive) cationic peptide active agent, said method comprising forming a composition of said peptide active agent, at least one neutral structure forming amphiphile, at least one anionic structure forming amphiphile or salt thereof, and optionally at least one solvent and orally administering said composition, wherein said composition comprises non-lamellar phase (especially particles thereof) and/or forms non-lamellar phase (especially particles thereof) on exposure to body fluids and wherein oral delivery is measured as blood plasma concentration relative to intravenous administration.

In methods and compositions having enhanced oral bioavailability, at least 1% of the peptide active agent concentration is present in the blood stream, relative to the amount measurable when administered intravenously, especially in saline solution. It is preferable that this availability be at least 1.5%, more preferably at least 2% and most preferably at least 3%. Very high peptide bioavailability (e.g. 5% or more) is also possible with the present compositions.

In a further aspect, the invention also provides for the use of a composition comprising a protease-sensitive (e.g. carboxpeptidase C-sensitive) cationic peptide active agent, at least one neutral structure forming amphiphile, at least one anionic structure forming amphiphile or salt thereof and optionally at least one solvent in the protection of said peptide active agent from enzymic degradation upon oral, intramuscular or subcutaneous administration, wherein said composition comprises particles of non-lamellar phase and/or forms particles of non-lamellar phase on exposure to body fluids.

In a yet further aspect, the invention also provides a method for the formation of a composition of the invention comprising forming particles of non-lamellar phase and/or particles which generate non-lamellar phase on exposure to body fluids, said particles comprising at least one neutral structure forming amphiphile, at least one anionic structure forming amphiphile or salt thereof and optionally at least one solvent, and subsequently contacting said particles with a solution of cationic peptide active agent. The method may also comprise the step of drying the resulting peptide-containing dispersion, for example by freeze drying or spray drying.

Without being bound by theory, it is believed that the increased bioavailability of the cationic peptides administered as compositions of the present invention is due at least in part to reduced enzymic degradation. In particular, the inventors have shown that not only do non-lamellar particulate formulations provide significant protection for peptides against proteolytic enzymes, but also that such non-lamellar formulations comprising anionic amphiphiles, and particularly fatty acids, are significantly more effective in such protection than are other formulations.

The action of proteolytic enzymes such as trypsin in degrading cationic peptides has been shown to be significantly reduced by formulations comprising fatty acids according to the present invention. This reduction in enzymic degradation results in a greater proportion of the peptide active agent reaching its site of absorption and crossing into the blood stream. It has been confirmed in animals that the level of peptide absorbed according to the present invention is noticeably higher than in the absence of these protective effects (see examples below).

In the present invention, the peptide active agents are generally cationic peptides or proteins and may range from small oligomers (such as di-, tri- or tetra-peptides) to large proteins with a molecular weight of many thousands of Daltons. All are referred to herein as "peptides" regardless of their secondary or tertiary structure. The peptides referred to herein will, however not generally be lipoproteins unless specifically indicated. Similarly, the terms "protease" and "peptidase" are used herein as equivalent unless otherwise indicated.

Peptides may consist purely of the 20 common α-amino acids of the "genetic code" (and optionally their stereoisomers) or may contain at least one other naturally occurring or non-naturally occurring amino acid unit such as β-, γ-, or δ-amino acids or the substituted equivalents of any of these, as well as alpha-amino acids not routinely found in natural proteins. Common substituents include hydrocarbyl substituents (e.g. alkyl, alkenyl, alkynyl, aryl, aralkyl, or alkaryl groups), heterocyclic substituents (e.g. nitrogen, oxygen or sulphur containing mono- or polycyclic substituents), nitrogen-based substituents (e.g. amino, alkyl amino, nitro, urea or azo substituents), sulphur-based substituents (e.g. thio, thioalkyl, or sulphonyl substituents), halogen-based substituents (e.g. fluoro, chloro, bromo or iodo, chlorate, iodate etc.), oxygen-based substituents (such as keto, carboxy, ester, hydroxy or aldehyde, peroxide, ether substituents) and combinations thereof. Obviously, certain natural and non-natural substituents are capable of bridging/crosslinking and frequently disulphide, ester, amide or other bridges may be present. Such crosslinks will reduce the conformational freedom of the peptides and frequently provide a more pronounced biological effect. Octreotide is an example of a peptide having a Cys-Cys crosslink and two amino-acids present in as their non-usual stereoisomers in the structure:

The formulation of the various components in the present invention may be carried out by known methods using the indicated amphiphilic components and peptide active agents. Suitable methods include those indicated in the present Examples and in U.S. Pat. No. 5,531,925, WO 02/02716, WO 02/068561, WO 02/066014 and WO 02/068562. The disclosures of these and all references cited herein are hereby incorporated herein by reference.

Dispersion methods include adding liquid crystal phase forming amphiphiles (with or without fragmentation agents) in dry, molten or solution form, to an aqueous solution (optionally including fragmentation agents and optionally including a lipid, such as phosphatidyl choline—PC) and either allowing natural fragmentation of the mixture or accelerating the process with, for example, mechanical agitation, vortexing, roto-stator mixing, high-pressure homogenation, microfluidisation and/or ultrasound.

The phase behaviour and size distribution of particulate formulations in the invention may also be controlled by one or more (preferably one) cycles of heating and cooling. Such cycles can be used to convert lamellar particles to non-lamellar form, and to reduce the spread of particle sizes. Where this method is used, the compositions should, preferably, be formulated such that the thermodynamically stable state is non-lamellar. Where heat cycling is used, the peptide active agent may be incorporated into the particles prior to and/or after heat cycling. Where more than one heat cycle is used, the active agent may also or alternatively be incorporated between cycles. Since peptide active agents are often heat sensitive, the active agent is preferably incorporated only after any heat cycling is complete. One notable exception to this is octreotide, which is relatively heat stable.

A heat cycle brings the composition, with or without the active agent present, up to a temperature sufficient to provide conversion of at least a portion of the particles to non-lamellar phase upon cooling to ambient temperature. This will typically involve heating to around 90-150° C. for 1-30 min followed by cooling to ambient temperature. More typically a heat cycle will involve heating to 100-120° C. for 2-20 minutes before cooling. The most suitable conditions will vary in detail between compositions but will be readily established by the skilled worker.

In the heat cycling process, the mean particle size typically increases but the distribution of particle sizes is reduced.

Where the peptide active agent is sufficiently heat stable, one or more heat cycles may be used to aid in loading of the active agent into particles of the composition of the invention. In particular, the stable level of active agent which may be loaded by means of heat cycling is often several times the equilibrium level when the components are incubated at room temperature. As a result, the method of synthesis of the invention preferably comprises a heat-cycling loading step where the active agent is stable under these conditions.

The presence of particles in non-lamellar form will preferably be assessed from a set of cryo-transmission electron microscopy particle images, preferably showing a sample of more than 30, preferably more than 50, and more preferably more than 100 particles. The presence of non-lamellar particles may also be assessed by X-ray scattering experiments.

The term "cationic" is used to indicate that the peptide active agents carry a net positive charge at the pH of the composition and/or at physiological pH. Generally, where the 20 amino acids commonly found in natural peptides and proteins dominate, a cationic peptide will have a greater number of basic amino acids such as lysine or arginine than acidic residues such as glutamic acid or aspartic acid.

In order to allow peptides not having an excess of basic functional groups to be used in the present invention, these peptides may be synthetically rendered "cationic", for example by protecting acid functional side-chains so that these cannot ionise. By this method, the charge-balance may be altered to provide peptide prodrugs with a net positive charge.

Where a potentially negatively charged group such as a carboxylic acid is protected, the protecting group should not affect the biological activity or should preferably be cleavable at the target site and should release a molecule with acceptable physiological properties. Ester and amide groups may both be used to prevent the ionisation of carboxylic acid moieties, for example, and both are cleavable chemically or enzymically within the body. It would also be preferable, for example, to protect an acid group as the ethyl or iso-propyl ester, so as to generate biologically tolerable ethanol or iso-propanol upon deprotection, rather than to use a methyl ester which would generate undesirable methanol.

In a similar way to the above, additional positive charge may be added to a peptide not having a sufficient cationic nature by provision of additional amine, or other groups having a positive charge at an appropriate pH. A serine or other hydroxy-containing reside might, for example, be esterified to the carboxy group of an amino-acid (especially a natural amino acid such as glycine or alanine) so that the amino group provides an additional basic moiety. A similar reaction may be carried out with a free thiol group of a cystine, which might be attached by means of a disulphide bond to an amino thiol. As with the protection of acid groups, the "activation" of neutral groups in this way will preferably be by means of bonds which may be cleaved (e.g. enzymatically) at the target site so as to release molecules which are biologically tolerable (such as glycine or alanine in the above example). Methods for forming many suitable substitutions are well known in the art. References herein to peptide active agents also refer to their "prodrugs" such as those described above, unless otherwise indicated.

The cationic peptide active agent will typically be of pharmaceutical or veterinary activity (such as a therapeutic, a vaccine, a prophylactic or a diagnostic agent) but may also be a dietary or cosmetic agent or a general stimulant or immune-boosting agent. More than one cationic peptide active agent may be incorporated if appropriate and additional active agents, including peptides and non-peptides, may be incorporated into the formulations as appropriate. Any additional active agent may be present to reinforce the activity of the cationic peptide active agent or may be provided to, for example, further increase the uptake of the cationic peptide or to suppress one or more undesirable effects of the cationic peptide active agent. In one preferred embodiment of the invention, the cationic peptide active agent is formulated in accordance with the invention in the presence of at least one protease inhibitor. By formulation with a protease inhibitor, the protective effect of the invention is further strengthened and a still greater proportion of the peptide active agent is delivered. Suitable protease inhibitors include pepsin inhibitors, trypsin inhibitors and chymotrypsin inhibitors, such as Trasylol® (aprotinin), amastatin, leupeptinebovine pancreatic trypsin inhibitor, ecotin, Streptomyces pepsin inhibitor, pepstatin, acetic acid chymotrypsin inhibitor I etc.

Generally, the cationic peptide active referred to in the present invention will be "enzyme sensitive" or "peptidase sensitive". As used herein, this indicates that at least one of the peptide bonds forming the peptide is susceptible to cleavage by proteolytic enzymes. Sensitivity to such enzymes may be measured by standard in vitro methods which will be familiar to those of skill in the art. Such methods are similar to those indicated in the Examples below for in vitro testing of the stabilising effect of the present invention. Typically, the peptides in the present invention will be sensitive to at least one peptidase and/or protease occurring in the mammalian gastro-intestinal tract such as trypsin, carboxpeptidase C, chymotrypsin, or pepsin. Preferably, the cationic peptide active agents are carboxpeptidase C sensitive.

As use herein, the term "non-lamellar" is used to indicate a normal or reversed liquid crystalline phase (such as a cubic or hexagonal phase) or the $L_3$ phase or any combination thereof. Where a particle is described as having a non-lamellar phase or form, this indicates that amphiphiles in at least the internal region of the particle should adopt this form. The particles will generally have two distinct regions, an internal region and a surrounding surface region. The surface region, even in a "non-familiar" particle will typically be lamellar, $L_3$ or crystalline. In contrast, a "lamellar" particle, as described herein is a particle having a solvent, rather than non-lamellar, core-region. Preferred non-lamellar forms are reversed liquid crystalline phases such as cubic or hexagonal phases. A highly preferred liquid crystalline phase is the reversed hexagonal phase.

A composition is considered "non-lamellar" if a molecular fraction of at least 30% of the structure forming amphiphile exists as non-lamellar phase particles. Similarly, a composition forms non-lamellar phase particles if at least 30% of the amphiphile is in the form of such phases after exposure to an aqueous fluid. This will generally be at least 50% in both cases and preferably at least 70% of the amphiphilic component should be in a non-lamellar form, either in the composition as formulated or after exposure to a body fluid. More preferably this is at least 80%, most preferably 90% or more.

Compositions which form non-lamellar phases on exposure to body fluids (compositions precursors) will generally contain ampliphilic, active peptide and optionally fragmentation components in similar relative proportions to the non-lamellar dispersions themselves but will typically have a lower proportion of the optional solvent. This solvent is generally aqueous or miscible with water and the composition precursors may be formed by drying non-lamellar compositions, for example by spray-drying or freeze drying. The precursors may also contain components such as sugars (e.g. lactose) to help stabilise and protect the compositions upon drying and/or to aid rehydration. Water miscible solvents are typically biologically acceptable and include alcohols (especially ethanol and isopropanol), glycerol, ethylene/propylene glycol (especially oligo-ethylene and/or propylene glycol) and short-chain mono glycerides (e.g. up to $C_6$, especially straight chain propyl, butyl, pentyl or hexyl optionally with one or more unsaturations).

Dispersions containing active ingredients and particularly those for intravenous administration to the human or animal body are desirably colloidal, that is they should be of a particle size no greater than 10 µm, especially no greater than 5 µm and particularly no greater than 1 µm. If particles within the dispersion exceed this size then the dispersion may not be colloidally stable and there is a considerable risk of causing embolism when the preparation is administered intravenously. Furthermore, it is desirable that the distribution of particle sizes be narrow to maximise control over the release of any active agent.

In the present case, compositions will often be administered by a method other than intravenously (especially orally, intramuscularly or subcutaneously), and thus the particle size need not be colloidal. In such cases, typical particle sizes range from around 10 µm to around 200 µm. It remains, however, advantageous for particulate compositions to provide well characterised and reproducible particle size distributions in order to control the rate of decomposition of the particles and/or release of the active agents.

In one embodiment of the invention, a "depot" is formed in vivo by administration of the composition of the invention. The depot will comprise a non-lamellar phase structure, generally formed at least in part after administration (e.g. by dissipation of a water miscible solvent and/or absorption of water). Depot compositions may form particles of non-lamellar phase as considered above but may, and more preferably will, form bulk non-lamellar phase. This may be considered to be a structure comprising continuous or semi-continuous "particles" of non-lamellar phase at least 0.5 mm in their largest dimension, preferably at least 1 mm and more preferably 5 mm or more. These bulk phases may release the active agent gradually, either directly into solution (e.g by means of degredation at the edges of the bulk phase) or by means of releasing smaller particles of non-lamellar phase as they degrade and these particles then serving to release the bulk of the active agent.

The "structure forming amphiphile" as indicated herein includes any agents that are capable of forming a structured phase in the presence of an aqueous solvent, optionally in the presence of other agents such as other amphiphiles and/or fragmentation agents. The amphiphiles will have at least one polar, hydrophilic group and at least one non-polar, hydrophobic group.

Examples of polar groups are well known (see e.g. U.S. published patent application number 20020153509) and include anionic groups such as carboxylates, phosphonates, sulphates and sulphonates, non-ionic groups such as alcohols, polyols (eg sugars, glycerol etc) and esters, cationic groups such as quaternary ammonium compounds, pyridinium salts and quaternary phosphonium salts and zwitterionic groups such as phospholipid head groups (e.g phosphatidyl-choline etc.), ammonioacetates, ammonio-alkanesulphonates and tri-alkylaminoalkylphosphate esters. The neutral amphiphile component will have no net charge at the pH of the composition and/or physiological pH while the anionic lipid component will carry a net negative charge under such conditions. Preferably, the neutral amphiphile component will be non-ionic. Furthermore, the anionic lipid will preferably include at least one acid group, or salt thereof, particularly a carboxylic acid group. Cationic amphiphilic components are not preferred and where present, there will be a greater quantity of anionic amphiphiles than cationic amphiphiles.

Examples of non-polar groups include $C_6$-$C_{32}$ alkyl and alkenyl groups, which are typically present as the esters of long chain carboxylic acids. These are often described by reference to the number of carbon atoms and the number of unsaturations in the carbon chain. Thus, CX:Z indicates a hydrocarbon chain having X carbon atoms and Z unsaturations. Examples particularly include caproyl (C6:0), caployl (C8:0), capryl (C10:0), lauroyl (C12:0), myristoyl (C14:0), palmitoyl (C16:0), phytanoly (C16:0), palmitoleoyl (C16:1), stearoyl (C18:0), oleoyl (C18:1), elaidoyl (C18:1), linoleoyl (C18:2), linolenoyl (C18:3), arachidonoyl (C20:4), behenoyl (C22:0) and lignoceroyl (C24:9) groups. An amphiphile will typically have one or two non-polar "tail" groups (mono-acyl and di-acyl lipids respectively) but may have three, four or more hydrophobic groups.

Examples of amphiphiles suitable for use in the present invention include natural lipids, synthetic lipids, surfactants, copolymers, proteins (in particular caseins and albumin), hydrotropes, alcohols, and other additives that may form or facilitate formation of structured phases. Preferred agents are glycerides (e.g. monoglycerides, diglycerides, and triglycerides), di- and polyglycerolesters of glycerides (e.g. diglycerol monooleate, diglycerol monocaprate), natural fats and oils (e.g. soybean oil, coconut oil, corn oil, castor oil, sunflower oil), fractionated oils (e.g. fractionated coconut oil, Miglyol® (Condea)), transesterified oils (e.g. Maizine®), transesterification products of oils and PEG (e.g. ethoxylated castor oil (e.g. Cremophor® EL (BASF)), ethoxylated hydrogenated castor oil (e.g. Cremophor® RH-40 (BASF)), ethoxylated corn oil (e.g. Labrafil® M2125 CS (Gattefossé))), acetylated monoglycerides, fatty acids (e.g. C6-C26 saturated and unsaturated fatty acids), fatty alcohols (e.g. phytantriol (3,7, 11,15-tetramethyl-1,2,3-hexadecantriol)), ether lipids (e.g. monooleyl glyceryl ether), natural and synthetic phospholipids (e.g. egg lecithin, soya lecithin, hydroxylated lecithin, phosphatidyl choline, phosphatidyl ethanolamine, phosphatidyl serine, phosphatidyl glycerol, phosphatidic acid), lyso-phospholipids (e.g. lyso-lecithin, lyso-phosphatidyl choline, lyso-oleyl phosphatidyl choline), phospholipid-analogous compounds (e.g. those disclosed in U.S. Pat. No. 6,344,576), sterols and sterol derivatives (e.g. cholesterol, sitosterol, lanesterol and their esters, especially with PEG or fatty acids), galactolipids (e.g. digalactosyl diacylglycerol, monogalactosyl diacylglycerol), sphingolipids (e.g. sphingomyelin); non-ionic surfactants, in particular ethoxylated surfactants such as PEG-fatty acid mono- and diesters (e.g. of the Crodet® (Croda), Cithrol® (Croda), Nikkol® Nikko), Myrj® (ICI series, Solutot® HS 15 (BASF)), PEG glycerol fatty acid esters (e.g. Tagat® L and O (Goldschmidt), Glycerox® L series (Croda), Capmul® EMG (Abitec)), transesterification products of oils and PEG (e.g. of the Labrafil® (Gattefossé), Cremophor® (BASF) Crovol® (Croda) and Nikkol® HCO (Nikko) series), PEG-sorbitan fatty acid esters (e.g. Tween® °, Tween® 80 and other polysorbates of the Tween® series (ICI)), PEG alkyl esters (e.g. of the Brij® (ICI) and Volpo® (Croda) series), PEG alkyl phenol surfactants (e.g. of the Triton X and N series (Rohm & Haas); polyglycerised fatty acids (e.g. Nikkol® Decaglyn (Nikko), Plurol® Oleique (Gattefossé)), propylene glycol fatty acid esters), propylene glycol fatty acid esters (e.g. Capryol® 90 (Gattefossé), Lutrol® OP2000 (BASF), Captex® (Abitec)), glycerol/propylene glycol fatty acid esters (e.g. Arlacel® 186 (ICI)), sorbitan fatty acid esters (e.g. of the Span® (ICI) and Crill® (Croda) series), sugar esters (e.g. of the SUCRO ESTER® (Gattefossé) and Crodesta® (Croda) series), polyoxyethylene-polyoxypropylene block copolymers (so-called poloxamers, e.g. of the Pluronic® (BASF), Synperonic® (ICI) and Lutrol® (BASF) series), copolymers of ethylene oxide and butylene oxide; anionic surfactants including fatty acid salts, bile salts (e.g. sodium cholate, sodium glycocholate, sodium taurocholate), carboxylates such as ether carboxylates, succinylated monoglycerides, mono/diacetylated tartaric acid esters of mono- and diglycerides, citric acid esters of mono- and diglycerides, glyceryl-lacto esters of fatty acids, acyl lactylates, alginate salts, propylene glycol alginate; cationic surfactants including ethoxylated amines (e.g. polyoxyethylene-15 coconut amine), betaines (e.g. N-lauryl-N,N-dimethylglycine), alkylpyridinium salts, quarternary ammonium salts such as hexadecyl triammonium bromide, decyl trimethyl ammonium bromide, cetyl trimethyl ammonium bromide; zwitterionic surfactants including trimethylammonio-ethylalkylphosphonates (e.g. the examples disclosed in U.S. Pat. No. 6,344,576); and all mixtures thereof.

The most preferred neutral structure-forming agents are glyceryl monooleate, glyceryl monolinoleate, glyceryl dioleate (GDO), dioleyl phosphatidyl ethanolamine (DOPE), dioleyl phosphatidylcholine (DOPC) and phytantriol, or lyso-phospholipids, especially lyso-oleyl phosphatidylcholine (LOPC). Any mixtures of these, particularly including GDO/DOPC or GDO:Egg lecithin (e.g. 70:30 wt/wt of either) are also suitable. Naturally occurring lipids from natural or synthetic sources are preferred due to their generally lower and/or more predictable toxicity profile. Naturally occuring fatty acid ester lipids including phospholipids are highly suitable.

Often the amphiphilic component will contain material in the form of extracted and purified natural products and will thus contain a mixture of related compounds. Soy bean phosphatidyl choline, for example, is a mixture of compounds having around 60-75% C18:2 acyl groups, around 12-16% C16:0 and the balance others. Similarly, commercial egg lecithin is typically around 70-75% phosphatidyl choline, around 10% phosphatidyl ethanolamine and the balance other lipids. Both of these products are suitable for use in the present invention. Different commercial preparations will also vary slightly but remain suitable.

An example of a preferred structuring agent for use in the present invention is commercially available glyceryl monooleate (GMO). As indicated above, this is largely monoglyceride with an oleoyl (C18:1) acyl chain but contains certain amounts of other compounds. These are included in the term "glyceryl monooleate" or "GMO" as used herein. Commercial preparations of GMO include GMOrphic-80 and Myverol 18-99 (available from Eastman Kodak), Rylo MG 19 and Dimodan DGMO (available from Danisco). Any of the structure-forming amphiphiles may be used alone or in combination with one or more other amphiphilic structuring agents.

A key component in the present invention is the anionic lipid component as this provides unexpectedly high levels of protection for the peptide active agent against enzymic degradation. Any anionic amphiphiles or combinations thereof may be used, including those indicated above, but it is preferred to use at least one fatty acid or fatty acid salt component. Preferred fatty acids are those corresponding to the fatty acid chains of natural ester lipids, including caproic, caprylic, capric, lauric, myristic, palmitic, phytanic, palmitolic, stearic, oleic, elaidic, linoleic, linolenic, arachidonic, behenic or lignoceric acids, their salts or mixtures thereof. The salts of fatty acids will be physiologically tolerable salts. The most preferred anionic amphiphiles are unsaturated naturally occurring fatty acids and their salts, especially oleic acid or salts thereof.

Preferred salts of any of the anionic components indicated herein, particularly the anionic amphiphiles, include alkali and alkaline earth metal salts as well as ammonium and alkylammonium salts. Preferred examples of these include sodium, potassium, lithium, calcium or magnesium salts, ammonium salts or triethylammonium salts. Where an anionic component or an acid is indicated herein, that indication refers also to physiologically tolerable salts thereof, unless specifically stated otherwise.

The anionic component will be present at a sufficient concentration to increase the bioavailability of the cationic peptide. Very high concentrations of anionic amphiphiles such as fatty acids are not always desirable, however, from the point of view of other important performance criteria including biocompatibility, dispersability, morphology and colloidal stability, as well as the health of the subject. Thus, in some embodiments, the anionic component will be present in a quantity not significantly greater than necessary to provide the desired level of enzyme protection. Generally the anionic component will be present in a concentration sufficient to increase the half-life of the (cationic) peptide active agent in carboxypeptidase C solution in vitro by at least 50% relative to the equivalent composition in the absence of the anionic component. More preferably, this half-life will increase by at least 75% or 100% and most preferably, will be 2.5, 3 or 4 times the value measured in the absence of anionic amphiphile.

The concentration of anionic amphiphile necessary will be readily determinable by simple experimentation, particularly with reference to the Examples herein and up to at least 50% anionic component may be used, as indicated below. Typically, however, the proportion of anionic amphiphile to neutral amphiphile will be 0.5-20% w/w concentration range and more preferably between 1-10% w/w. The most preferred range is between 2 and 8% w/w.

Preferably the particulate dispersions referred to herein contain at least one fragmentation agent. The fragmentation agent serves to improve the dispersability of the non-lamellar phase, forms a stabilising phase around the non-lamellar particle and/or stabilises the dispersion. Suitable fragmentation agents will be agents which aid the dispersal of amphiphile into particles (especially non-lamellar phase particles) or stabilise such particles. Typically a fragmentation agent will be a surfactant such as an amphiphilic block copolymer.

Important fragmentation agents include natural lipids, synthetic lipids, surfactants, copolymers, proteins (in particular caseins and albumin), hydrotropes, alcohols and other additives that may facilitate fragmentation spontaneously or with the aid of externally applied forces and pressures and contribute to stabilisation. This includes also nanoparticles and combinations of polymer and nanoparticles (see e.g. WO 99/12640).

Preferred fragmentation agents are copolymers and these may have blocks comprising polyoxyalkylenes, polyvinylpyrrollidone, polyvinylacetate, polyvinylalcohol, polyesters, polyamides and/or polyalkenes. The block copolymer will comprise at least two blocks of polymer having different degrees of hydrophilicity. Certain proteins (such as casein) are also of amphiphilic character and may be used as fragmentation agents. Where the cationic peptide active agent is an amphiphilic protein, this may act as both the active agent and the fragmentation agent, or may be included in addition to another active agent and/or fragmentation agent.

Preferred examples of amphiphilic block copolymers are poloxamers, which comprise at least one block of polyoxyethylene and at least one block of polyoxypropylene. The most preferred fragmentation agents are poloxamer 407 (e.g. Pluronic® (Lutrol) F127, BASF), poloxamer 188 (e.g. Pluronic® F68, BASF), and polysorbate 80 (e.g. Tween® 80, ICI).

Where included to aid dispersion, the fragmentation agent will be present at a level sufficient to bring about the fragmentation of the composition and/or to stabilise the fragmented particles (which will preferably be non-lamellar phase). Such fragmentation may be spontaneous or may require physical fragmentation such as by sheering and/or ultrasonication. It is preferable that sufficient fragmentation agent is present that the composition is physically stable. Typically a fragmentation will provide a desired effect at a level of 1-30% by weight, relative to the total amphiphile content of the composition. This will more typically be 5-15% by weight and most preferably 8-12% by weight.

Active agents suitable for the present invention are natural and synthetic cationic peptides and include human and veterinary drugs and vaccines, diagnostic agents, cosmetic agents, nutrients, dietary supplements etc. These may be inherently cationic or may be rendered cationic by appropriate synthetic protection or activation as discussed supra. They may also comprise non-natural amino acids as indicated above.

Examples of suitable drugs include antibacterial agents including macrocyclic peptide antibiotics, anti fungal agents, anticancer and/or anti viral agents, anti inflammatorys, cardiovascular drugs including cholesterol lowering and blood-pressure lowing agents, analgesics, antidepressants, hormones, vaccines and bone modulators. Diagnostic agents include radionuclide labelled compounds and contrast agents including X-ray enhancing agents such as iodinated compounds and gamma-radiation emitting compounds. Nutrients include dietary supplements etc.

Preferred active agents include human and veterinary peptide drugs selected from the group consisting of adrenocorticotropic hormone (ACTH) and its fragments, angiotensin and its related peptides, antibodies and their fragments, antigens and their fragments, atrial natriuretic peptides, bioadhesive peptides, Bradykinins and their related peptides, calcitonins and their related peptides, cell surface receptor protein fragments, chemotactic peptides, cyclosporins, cytokines, Dynorphins and their related peptides, endorphins and P-lidotropin fragments, enkephalin and their related proteins, enzyme inhibitors, fibronectin fragments and their related peptides, gastrointestinal peptides, growth hormone releasing peptides, immunostimulating peptides, interleukins, luthenizing hormone releasing hormones (LHRH) and their related peptides, melanocyte stimulating hormones and their related peptides, nuclear localization signal related peptides, neurotensins and their related peptides, neurotransmitter peptides, opioid peptides, oxytocins, vasopressins and their related peptides (especially desmopressin), parathyroid hormone and its fragments, protein kinases and their related peptides, somatostatins and their related peptides, substance P and its related peptides, transforming growth factors (TGF) and their related peptides, tumour necrosis factor fragments, toxins and toxoids and functional peptides such as anticancer peptides including angiostatins, antihypertension peptides, anti-blood clotting peptides, and antimicrobial peptides; selected from the group consisting of proteins such as immunoglobulins, angiogenins, bone morphogenic proteins, chemokines, colony stimulating factors (CSF), cytokines, growth factors, interferons, interleukins, leptins, leukemia inhibitory factors, stem cell factors, transforming growth factors and tumour necrosis factors, all derivatised as necessary to render them cationic.

Most preferably, the cationic peptide active agent will be inherently cationic, in that it will have a net positive charge at the pH of the formulation, without any chemical modification.

Some examples of peptide active agents, along with an outline of some of their properties and/or target indications is given below in Table 2. The table also shows the amino acid number and isoelectric point of certain peptides.

Preferred peptide active agents are cationic and this may be measured by the isoelectric pH of the peptide, e.g. in its active form and/or when modified as a prodrug (as described above). At a pH below the isoelectric value, a peptide can be considered cationic. Thus, preferred peptides will have an isoelectric point of at least 6.5, especially at least 7.0 (e.g. at least 7.5, preferably at least 7.8) and most preferably around 8 or more (e.g at least 8.0, at least 8.5 or at least 9.0). Calcitonin, for example has its isoelectric point at around pH 8.9 and vasopressin at around 8.0. The isoelectric point of octreotide is also around 8.0. Examples of all such peptides are given in Table 2. Correspondingly, the peptide active agents are preferably not peptides such as lepuridin or insulin α, which have a isoelectric values of around 4.

TABLE 2

Peptide and Protein Active Agents

| | Amino Acids | Isoelectric pH |
|---|---|---|
| 1a HORMONES & HORMONE DERIVATIVES | | |
| Somatotropin Growth hormone deficiency and for Turner's syndrome | 191 | 5.27 |

TABLE 2-continued

Peptide and Protein Active Agents

| | Amino Acids | Isoelectric pH |
|---|---|---|
| Somatostatin (& analogues) | 28 | 9.58 |
| Acromegaly and carcinoid and vasoactive intestinal peptide tumours | | |
| Calcitonin (salmon) | 32 | 8.86 |
| Osteoporosis | | |
| Oxytocin | 9 | 5.51 |
| induction of birth labour & maintenance of milk secretion | | |
| Gonadorelin | 10 | 8.75 |
| Ovulation control | | |
| Derivatives: Leuprolide; Goserelin; Triptorelin | | |
| Vassopresin | 9 | 8.06 |
| Diabetes insipidus, haemorrhaging esophageal varices, etc. | | |
| Derivatives: Desmopressin, Felypressin | | |
| Follitropin-beta | 111 | 5.91 |
| Infertility | | |
| Follitropin-alpha | 116 | 8.38 |
| Infertility | | |
| human Chorionic Gonadotropin-beta | 145 | 8.65 |
| Infertility | | |
| Thyrotropin alpha | 92 | 8.38 |
| adjunctive diagnostic tool for serum thyroglobulin | | |
| Secretin (e.g. swine) | 27 | 9.45 |
| pancreatic assessment | | |
| Bradykinin | 9 | |
| hypotensive tissue hormone | | |
| Insulin α | 21 | 3.79 |
| Insulin β | 30 | 6.9 |
| 1b ANTIVIRAL, ANTIBACTERIAL & ANTIFUNGAL | | |
| Interferon-alpha 1/13 | 166 | 5.18 |
| Interferon-alpha 2 | 165 | 5.99 |
| Interferon-beta | 166 | 8.93 |
| Interferon-gamma | 166 | 9.54 |
| In different recombinant forms, anti-hepatitis C, leukemia, sclerosis | | |
| Tachyplesin I | 17 | 9.93 |
| antibacterial, antiviral | | |
| Tuftsin | 4 | 11 |
| immunomodulator, antimicrobial, antiviral, anticancer | | |
| Magainin I | 23 | 10 |
| Magainin II | 23 | 10 |
| Inhibit the growth of numerous bacteria and fungi | | |
| Indolicidin (e.g. bovine) | 13 | 12.01 |
| antibacterial, antifungal, anticancer, antiviral, antiparasite | | |
| Protegrin (e.g. swine) | 18 | 10.66 |
| antibacterial, antifungal, antiviral | | |
| Polyphemusin I | 18 | 10.33 |
| Polyphemusin II | 18 | 10.1 |
| antibacterial, antifungal, antiviral | | |
| Polymixin B | | |
| antibacterial | | |
| Gramicidin S | 10 | |
| antifungal | | |
| 1c OTHER PEPTIDES & PROTEINS | | |
| Intercellular Adhesion Molecule 1 | 23 | 9.51 |
| Pneumadin | 10 | 4.36 |
| antidiuretic | | |
| Alteplase | 527 | 7.61 |
| Acute myocardial infarction and acute ischiemic stroke | | |
| Interleukin-1 receptor antagonist | 550 | 8.51 |
| anti rheumatoid arthritis | | |
| GMCSF | 127 | 5.21 |
| Filgrastim (G-CSF) | 177 | 5.43 |
| neutropenia | | |
| Lepirudin | 65 | 4.04 |
| anticoagulant | | |
| Becaplermin | 109 | 9.38 |
| Diabetic foot ulcers | | |
| OspA | 257 | 6.72 |
| Prevention of Lyme disease | | |
| Avicine | 37 | 4.58 |
| Anticancer | | |
| Tubulysins A–F | | |
| anticancer | | |
| Contakulin G (CGX-1160) | | |
| analgesic | | |
| alpha conotoxin-like peptides | 16 | |
| analgesic (see WO 02/079236) | | |
| Mellitin | 26 | 12.02 |
| analgesic, antibacterial | | |
| 1d INTERLEUKINS (ILs) | | |
| IL-1alpha | 159 | 5.3 |
| Hematopoietin-1 | | |
| IL-1 beta | 153 | 5.91 |
| Catabolin | | |
| IL-2 | 133 | 7.05 |
| T-cell growth factor (TCGF) (Aldesleukin). | | |
| IL-3 | 133 | 6.97 |
| Haematopoietic growth factor | | |
| IL-4 | 129 | 9.26 |
| B-cell stimulatory factor | | |
| IL-5 | 115 | 7.02 |
| T-cell replacing factor | | |
| IL-6 | 183 | 6.21 |
| B-cell stimulatory factor | | |
| IL-7 | 152 | 8.72 |
| IL-8 | 77 | 9.24 |
| Neutrophil-activating | | |
| IL-9 | 126 | |
| T-cell growth factor P40 | | |
| IL-10 | 160 | 7.63 |
| Cytokine synthesis inhibitory factor | | |
| IL-11 | 178 | 11.16 |
| Adipogenesis inhibitory factor | | |
| IL-13 | 112 | 8.81 |
| IL-15 | 114 | 4.52 |
| IL-17 | 132 | 8.62 |
| Cytotoxic T lymphocyte-associated antigen 8 | | |
| IL-18 | 157 | 5.04 |
| Interferon-gamma inducing factor | | |
| IL-19 | 153 | 7.8 |
| Melanoma differentiation associated protein-like protein | | |
| IL-20 | 152 | 8.77 |
| Four alpha helix cytokine ZCYTO10 | | |
| IL-24 | 158 | 8.6 |
| Melanoma differentiation associated protein 7 | | |
| IL-26 | 150 | 9.99 |

Preferred examples, particularly from this list, include Somatostatin (and analogues including octreotide), Calcitonin (salmon), Gonadorelin, Vassopresin, Follitropin-alpha, human Chorionic Gonadotropin-beta hCG-beta, Insulin and Insulin analogues, Thyrotropin alpha, Secretin, Bradykinin, Interferon-beta, Interferon-gamma, Tachyplesin I, Tuftsin, Magainin I, Magainin II, Indolicidin, Protegrin, Polyphemusin I, Polyphemusin II, Polymixin B, Gramicidin S, Intercellular Adhesion Molecule 1, Alteplase, Interleukin-1 receptor antagonist, Becaplermin, Tubulysins A-F, Contakulin G (CGX-1160), alpha conotoxin-like peptides, Mellitin, IL-2, IL-3, IL-4, IL-5, IL-7, IL-8, IL-9, IL-10, IL-11, IL-13, IL-17, IL-19, IL-20, IL-24 and IL-26. The most preferred cationic peptide active agents are the inherently cationic peptides calcitonin (human or preferably salmon), octreotide and other somatostatin analogues (such as those disclosed and referred to by Janecka et al. in Endocrine Regulations 35 75-79, 2001) and desmopressin.

Compositions of the present invention may be formulated as pharmaceuticals by methods well known in the art. These formulations will typically be oral formulation such as tablets, coated tablets (such as controlled release tablets), capsules, suspensions, dispersions, syrups, or powders, but may be formulations for inhalation (such as powders or aerosols), or for parenteral (e.g subcutaneous, intramuscular or intravenous) administration in the form of, for example, sterile dispersions in saline, or precursors thereof. One particularly interesting embodiment relating to parenteral "depot" administration is described in detail below.

The compositions may be formulated with conventional pharmaceutical carriers, diluents and/or excipients such as aqueous carriers (e.g. water for injections), solvents, binders, fillers, stabilizers, osmolality adjusting agents, effervescing agents, pH buffers and modifiers, viscosity modifiers, sweeteners, lubricants, emulsifiers, flavours, coating agents (e.g. gastric juice resistant coatings) etc. Formulations comprising at least one pharmaceutically acceptable carrier and/or diluent thus form a further preferred aspect of the invention.

The dosage of the compositions of the invention to be administered to a subject will be dependent upon the active agent, the species, size, maturity, health and condition of the subject and upon the formulation chosen. The compositions may also deliver a larger proportion of the active agent to the subject than traditional formulations and this should be taken into account. Suitable dosages will be readily established for known therapeutic peptides by reference to the bioavailability when formulated in the compositions of the invention and the known dosage and bioavailability when delivered by established methods.

Alternatively, the compositions may be formulated as functional foods or beverages, in which situation the carriers and excipients will typically comprise edible food or beverage products. Such products may be processed foods for consumption hot, such as ready meals, but will more preferably be cold foods including spreads (e.g margarine or low-fat spreads), soft drinks, breakfast cereals, breakfast bars, breads, biscuits, ice creams, chilled desserts such as yoghurts, mousses or trifles, milk or milk based drinks.

Where the peptide active agents present in the compositions of the invention are formulated as functional foods or beverages, it will be important that the maximum dose which can be accidentally consumed by over-eating such foods is not excessive.

In one alternative embodiment of the invention, the compositions of the invention comprise or form a bulk non-lamellar phase structure, rather than particles of non-lamellar phase. This is a particularly suitable embodiment for the generation of "depot" compositions which gradually degrade in vivo releasing the peptide active agent either as a result of this degradation or by gradual diffusion (or both). Because the compositions of the invention are highly effective in protecting peptide active agents from degradation in vivo, these compositions make highly effective depot compositions and precursors. Generally, depot compositions are administered parenterally, especially by intramuscular or subcutaneous injection and may result in release of the active peptide over a period of days (e.g. 1 to 14 days), weeks (e.g. 2-8 weeks) or even several months (e.g. 1-3 months).

In a depot embodiment, it is generally preferable that the compositions do not adopt a non-lamellar phase structure at the time of administration. This is because bulk non-lamellar phases (as opposed to particles) are often viscous and difficult or painful to inject. As a result, in this embodiment, the compositions typically contain around 0.5 to 50% by weight of an oxygen-containing organic solvent such as an alcohol, ketone, sulphoxide, ester or ether. The addition of such solvents allow the formation of a low-viscosity pre-formulation which will subsequently form a non-lamellar composition of the invention upon contact with body fluids. Obviously such pre-formulations are also compositions of the invention. In a preferred embodiment, the compositions of the invention thus further comprise 0.5 to 50%, preferably 2 to 30%, more preferably 5 to 20% by weight of an oxygen containing, biotollerable organic solvent. In this embodiment, it is preferable that the composition is not initially in the form of a non-lamellar phase, but forms such a phase (as described herein) upon contact with a body fluid after administration.

Typical solvents suitable for use in the compositions include at least one solvent selected from alcohols, ketones, esters (including lactones), ethers and sulphoxides. Examples of suitable alcohols include ethanol, isopropanol and glycerol formal. Examples of ketones include acetone and n-methyl pyrrolidinone. Suitable ethers include diethylether, glycofurol and dimethylisobarbide. Suitable esters include ethyl acetate and isopropyl acetate and dimethyl sulphide is as suitable sulphide solvent.

Where the composition is a depot composition or pre-formulation, it is preferable that the neutral amphiphilic component comprises a diacyl lipid, especially a diacyl glycerol, and a phospholipid in proportions 5:95 to 95:5 by weight, preferably 10:90 to 90:10 and more preferably 10:90 to 45:55 diacyl lipid:phospholipid.

Correspondingly, in a further embodiment, the present invention provides a method for administering a cationic peptide to a patient comprising injection of a composition of the invention comprising an organic solvent (as described herein) which subsequently forms a non-lamellar "depot" composition of the invention in vivo upon contact with a body fluid.

The invention will now be further illustrated by reference to the following non-limiting examples and the attached figures, in which.

EXAMPLES

The following abbreviations are used in the Examples below:

| | |
|---|---|
| E200 | Epikuron 200 (soya lecithin) |
| F127 | Pluronic ™ F127 (BASF) |
| GDO | Glycerol Di-Oleate |
| GMO | Glycerol Mono-Oleate |
| LA | Linoleic Acid |
| LD | Laser Diffraction |
| OA | Oleic Acid |
| PC | phosphatidyl choline |
| Ret Pal | Retinyl palmitate |
| SAXS | Small Angle X-ray Scattering |
| sCT | Calcitonin (Salmon) |
| TEM | Transmission Electron Microscopy |
| Try Gly | Tri-Glyceride |

Example 1

GMO/OA Particles

1.1—Preparation of a Dispersion Under High Pressure

A coarse dispersion of largely cubic particles was formed by mixing Rylo MG 19 GMO (Danisco, 4.70 g) and oleic acid (Apoteket, 0.24 g) and adding the mixture dropwise to poloxamer 147 (BASF, 0.5 g) in deionised water (45.7 g) under vigorous stirring at ambient temperature. The resulting coarse dispersion was allowed to equilibrate for about 30 minutes before homogenisation in a microfluidizer at high pressure (350 bar) for 10 min (6 cycles) at 40° C.

The particle size was measured using laser diffraction (Coulter LS230) before and after homogenisatin. The particle morphology and phase behaviour of the homogenisate was analysed using small angle X-ray scattering (SAXS), and by cryo-transmission electron microscopy (cryo-TEM).

The homogenisate was a colloidal dispersion with particle sizes below 1 μm consisting mainly of vesicles with a proportion of cubic-phase-cored particles. Particles prepared by this method were generally exposed to a heat treatment step prior to loading.

1.2—Preparation of a Dispersion Under High Pressure

The procedure of Example 1.1 was repeated, except that the homogenisation step was carried out at low pressure (174 bar) for a shorter period (5 cycles).

The low pressure method produced a larger proportion of cubic-phase-cored particles and some vesicles with a bi-modal particle size distribution. The homogenisate was optionally exposed to a cycle of heat treatment prior to loading.

1.3—Heat Treatment

An optional cycle of heat treatment is carried out on the non-lamellar dispersion prepared in Examples 1.1 and 1.2 so as to convert a larger proportion of the particles to non-lamellar phase. The particles of the method from Example 1.1 were usually treated with one cycle of heat treatment.

A sample of the dispersion generated in Example 1.1 or 1.2 (10 ml) was autoclaved (121° C., 20 min) and cooled to ambient temperature. When examined by cryo-TEM, a virtually all particles in the dispersion show non-lamellar character. The particle size distribution is also somewhat narrowed in comparison with the dispersion prior to heat treatment and the average particle size increased slightly. The heat-treated particles showed improved stability to storage.

Example 2

Further Non-Lamellar Dispersions and Loading

2.1—Compositions of Non-Lamellar Dispersions

Non-lamellar dispersions of varying components in water may be prepared by the method of Example 1.1 and optionally treated with the heat treatment method of Example 1.2. The resulting dispersion is analysed for particle size and phase behaviour.

TABLE 3

| No. | Neutral amphiphile(s) | wt %[1] | anionic amphiphile | wt %[1] | Fragmentation agent | wt %[1] | Water %[2] | Dominant Phase |
|---|---|---|---|---|---|---|---|---|
| 1 | GMO | 94 | OA | 5 | F127 | 1 | 91 | Cubic |
| 2 | GMO | 89 | OA | 20 | F127 | 1 | 91 | Hex[3] |
| 3 | GMO | 49.5 | OA | 49.5 | F127 | 1 | 91 | Hex[3] + $L_2$[4] |
| 4 | GMO | 94 | LA | 5 | F127 | 1 | 90 | Cubic |
| 5 | E200:GDO | 50:32 | OA | 5 | F127 | 13 | 90 | Hex[3] |
| 6 | GMO:Ret Pal | 73:12 | OA | 5 | F127 | 10 | 90 | Hex[3] |
| 7 | GMO:Tri Gly | 76:9 | OA | 5 | F127 | 10 | 91 | Hex[3] |
| 8 | E200:GDO | 51:33 | LA | 4 | F127 | 12 | 91 | Hex[3] |
| 9 | GMO:Ret Pal | 73:12 | LA | 5 | F127 | 12 | 91 | Hex[3] |

[1]Weight % of total amphiphile & fragmantation agent
[2]Weight % water in final dispersion
[3]Hex = Hexagonal phase
[4]Reversed micellar phase

2.2—Peptide Loading

To each of the dispersions of Example 2.1 is added the cationic peptide desmopressin to a final concentration of 1 mg/ml. The dispersion is allowed to equilibrate for 60 minutes at room temperature.

2.3 Peptide and Peptidase Inhibitor Loading

To each of the dispersions of Example 2.1 is added the cationic peptide calcitonin to a concentration of 0.8 mg/ml and one or more peptidase inhibitors selected from aprotinin (Trasylol®), amastatin and/or leupeptin to a total concentration of 0.4 mg/ml. The dispersion is allowed to stand for 3 hours at room temperature.

Example 3

Peptide Degradation by Protease Trypsin

3.1 Peptide Loading and Protease Assay Method

Salmon calcitonin (sCT) was dissolved into two vials with 0.9% saline solution and into one vial with the test non-lamellar dispersion in saline solution, to a concentration of 1 mg sCT/mL. The vials were placed in a water bath at 37° C. with stirring.

To one vial with sCT in saline was added an inhibitor, aprotinin (Trasylol®) (10 000 KIE/mL, 125 μL/mL/saline).

Zero samples were taken out from the two saline vials and from the non-lamellar-dispersion.

The protease Trypsin (500 μg/mL, 30 μL/mL saline) was added to all vials.

After fixed time intervals, samples were transferred to HPLC vials and the inhibitor Trasylol® added to the non-lamellar-dispersion samples and the samples in saline without Trasylol®.

To a 100 μL sample was added 230 μL methanol and between 40 and 115 μL chloroform (the volumes being adjusted depending upon the lipid composition and concentration of the non-lamellar-dispersion) so as to form a one phase system. The samples were mixed thoroughly and allowed to stand for five minutes.

The one phase system was split into two phases by adding 230 μL chloroform and 700 μL water. The samples were mixed and centrifuged for 5 min at 13 000 rpm. 200 μL of the upper water/methanol phase was transferred to a 300 μL insert vial.

Analysis of the amount of non-degraded peptide was performed using HPLC.

3.2 GMO/OA/sCT Comparative Protease Assay

The above loading and test procedure was repeated with non-lamellar dispersion samples containing a varying proportion of oleic acid (OA) as an anionic lipid component, prepared as indicated in Example 1.1 and 1.3 with NaCl added to a final concentration of 0.9% after heat treatment. The controls and non-lamellar-dispersions were treated with s-CT and Trasylol® in the concentrations given above in Example 3.1.

The non-lamellar phase was a GMO/OA non-lamellar liquid crystalline phase particle dispersion (d~1 μm) containing 9% lipid to water with GMO/OA ratios of 100/0, 95/5, and 50/50, and 1% polymeric stabiliser Pluronic™ F127 (BASF). Controls were saline solution without Trasylol® and saline solution with Trasylol® as indicated above.

Figure 1:
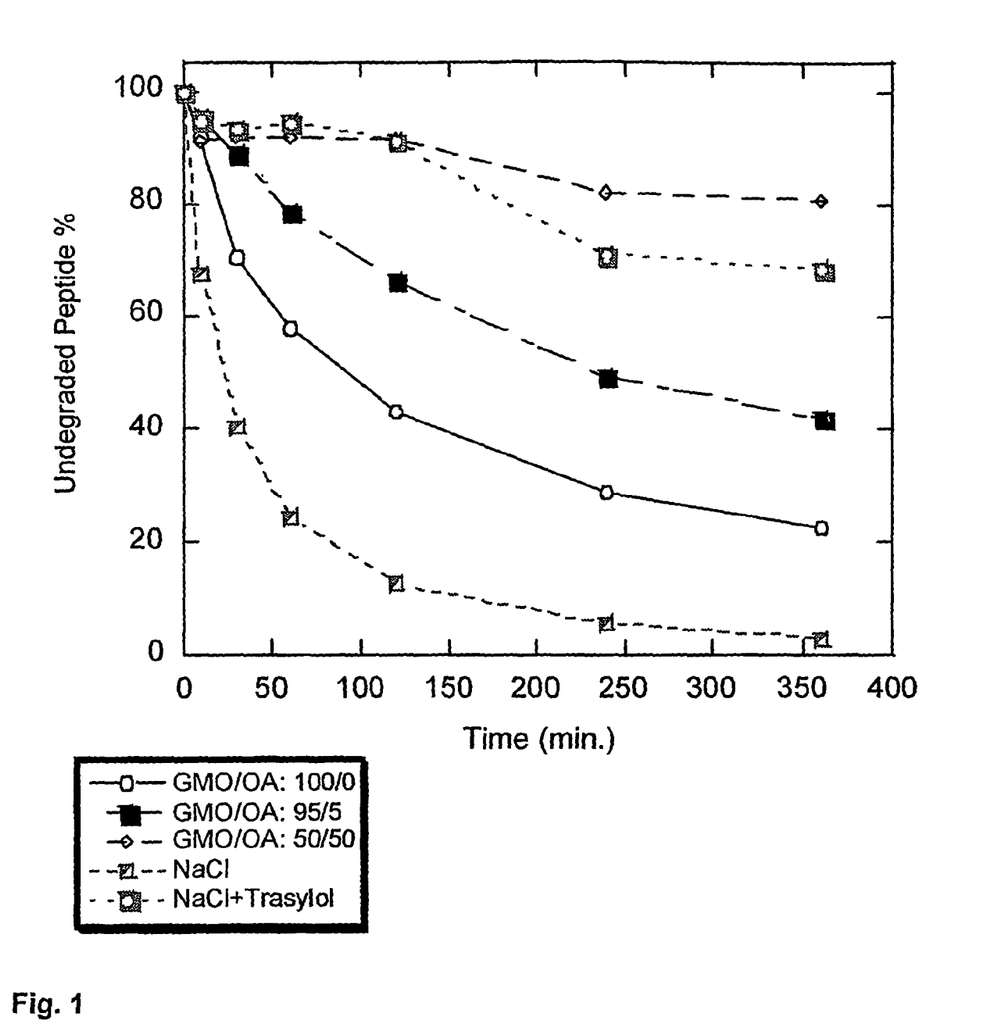
FIG. 1 Shows the proportion of peptide active agent Calcitonin remaining undegraded over time with different lipid formulations.

The results of the HPLC analysis are shown in FIG. 1, which clearly indicates that increasing the concentration of anionic amphiphile resulted in a decreased degradation rate of the sCT peptide active agent. The 50/50 GMO/OA dispersion may be seen to provide a greater degree of protection than is given even by the peptidase inhibitor Trasylol®.

Example 4

Animal Bioavailability Study 4.1—General Procedure

On the first day of the experiment, the rats were prepared by inserting a silicon catheter (OD approx. 1 mm) in the jugular vein under ketalar/xylazin anaesthesia. The catheter was tunnelled under the skin and exteriorised between the scapulae. After surgery the rats were allowed 48 hours of recovery before dosing. The catheter was rinsed with 0.9% NaCl containing 1 mM EDTA, every morning during the recovery period.

In the morning, after approximately 16 hours of fasting (water was accessible), the animals were dosed and blood collected. The animals were allowed free access to water after dosing, but had no access to food. After the last sampling, all animals were sacrificed.

Non-lamellar particular dispersions were prepared by the high pressure method of Example 1.1 followed by heat treatment as set out in Example 1.3 and calcitonin loading.

4.2—Dosing

The rats were dosed intravenously through the venous catheter or by gavage by a plastic ball-tipped gavage tube. Intravenously dosed rats were given 1 mg sCT per kg bwt in 0.5 mL/kg of a sterile acetate buffer and gavaged rats were given dispersions in water of sCT-containing non-lamellar dispersions to a dose of 0.5 mg sCT per kg bwt. Total non-lamellar dispersions and sCT concentrations were varied and the total oral dose volume ranged from 2.5 to 25 mg/kg bwt. Oral dosing was performed under light isoflurane anesthesia.

4.3—Sampling

Blood samples (0.5 mL) were collected pre-dose (one day before dosing), 10 minutes, 30 minutes, 1 hr, 3 hrs, 6 hrs and 24 hrs after dosing in EDTA-treated test tubes also containing 500 KIE aprotinin (Trasylol®) per mL sample. All blood samples were gently mixed and held on ice (maximally 10 minutes) before they were centrifuged at 2,000 g for 10 minutes at +4° C. Plasma were then immediately transferred to new test tubes and put on dry ice. Samples were stored at −80° C. until analysis.

4.4—Analysis

The content of sCT in all plasma samples was measured by a commercially available enzyme-linked immunoassay kit.

Plasma sCT concentration data were utilized to calculate area-under-the-curve from 0 to 6 hours (AUC) by the trapezoidal method.

Dose-corrected absolute bioavailability of sCT in the oral non-lamellar formulations were calculated as:

$$\text{Availability}(F) = (\text{AUC}_{oral} \times \text{Dose}_{IV}) / (\text{AUC}_{IV} \times \text{Dose}_{oral}) \times 100$$

4.5—Results

Figure 2:
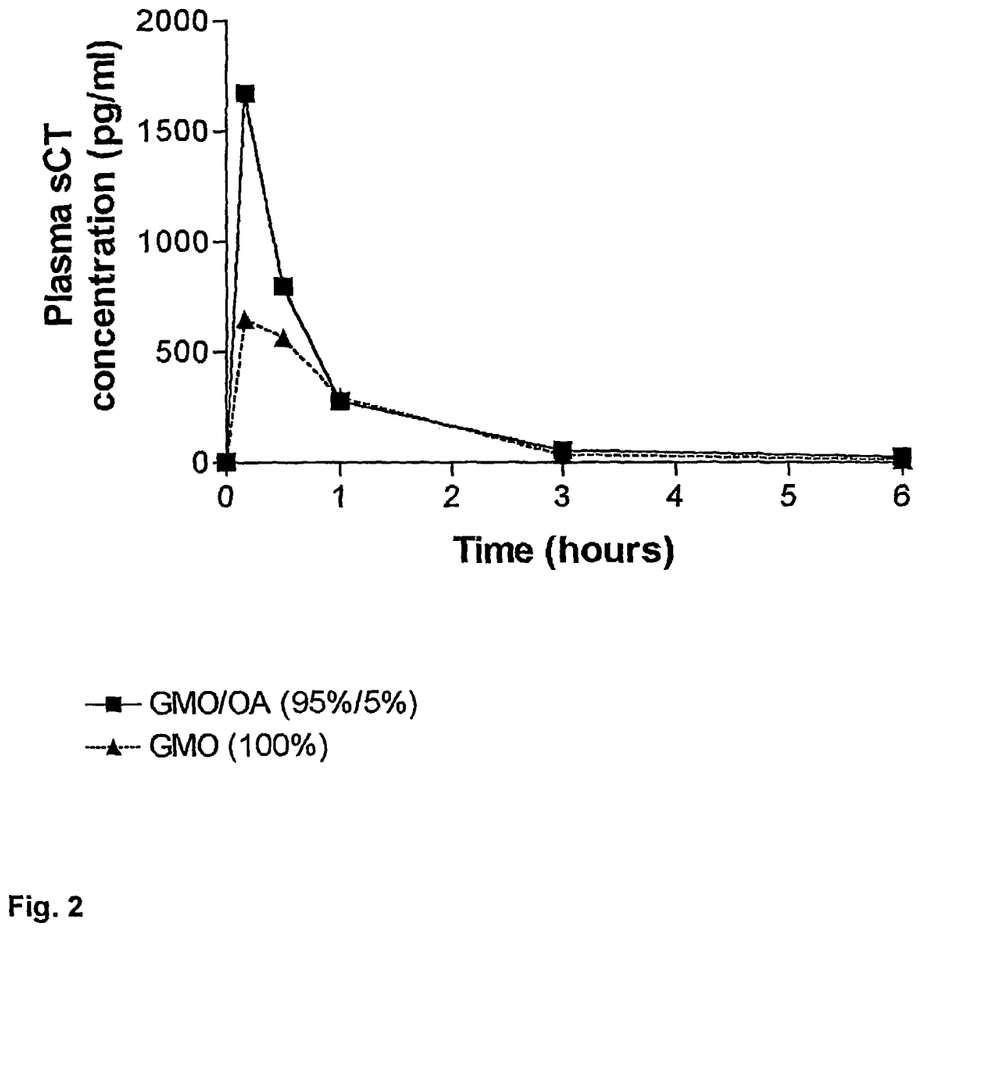
FIG. 2 Shows Plasma salmon Calcitonin (sCT) concentrations after oral delivery in GMO/OA (95%/5%) or GMO (100%) cubic liquid crystalline formulations.

Rats were dosed with an intravenous sCT solution, and orally with a GMO/OA (95%/5%) or GMO (100%) sCT non-lamellar dispersions, according to the above described method. All dispersions were predominantly cubic liquid-crystal dispersed phases. Plasma sCT contents were analysed and sCT plasma concentrations were plotted over time (FIG. 2). Absolute bioavailability (F) sCT administered orally in the GMO/OA formulation was around 1%, while sCT delivered in the pure GMO formulation resulted in bioavailability of approx. 0.5%. Hence, the GMO/OA (95%/5%) has an enhancing effect of around doubling the oral bioavailability of sCT compared to the non-lamellar GMO (100%) formulation.

Example 5

Depot Composition and In Vitro Phase Study

Injectable formulations containing phosphatidyl choline ("PC"—epicure 200) and glycerol dioleate (GDO) with and without the anionic lipid Oleic Acid (OA) and with EtOH as solvent were prepared to illustrate that liquid crystalline "depot" compositions can be accessed.

Appropriate amounts of PC and EtOH were weighed in glass vials and the mixture was placed on a shaker until the PC completely dissolved to form a clear liquid solution. GDO and optionally OA was then added to form an injectable homogenous solution.

The formulations were manufactured with compositions according to Table 4. A cationic peptide active substance, salmon calcitonin (sCT), was added to each formulation to a concentration of 500 μg sCT/g formulation. The formulations were designed as homogenous suspensions for parenteral administration (mixing required shortly prior to use since the drug is not completely dissolved in the PC/GDO/EtOH system). Formulation G contained OA.

The phase study in this example is performed in excess of rat serum at 37° C. in order to simulate an in vivo situation. Table 4 shows the same phases formed

TABLE 4

| Formulation | PC (wt %) | GDO (wt %) | OA (wt %) | EtOH (wt %) | Phase in rat serum |
|---|---|---|---|---|---|
| F | 36 | 54 | — | 10 | $I_{II}$ |
| G | 34 | 51 | 5 | 10 | $I_{II}$ |

$I_{II}$ = reversed cubic liquid crystalline phase
OA = Oleic Acid

Example 6

In vivo Release Study from Depot Formulations

Formulations F and G in Example 5 were used in an in vivo drug release study in rat. The formulations were administrated subcutaneously between the scapulae by using a syringe and the dose of sCT was 500 μg/kg body weight. The release profile was monitored for a period of 13 days. The sCT concentration in the rat plasma samples was analysed with a commercial kit from DSLabs. The drug was enzymatically amplified with sandwich-type immunoassay using biotin-streptavidin as detection system.

Figure 3:
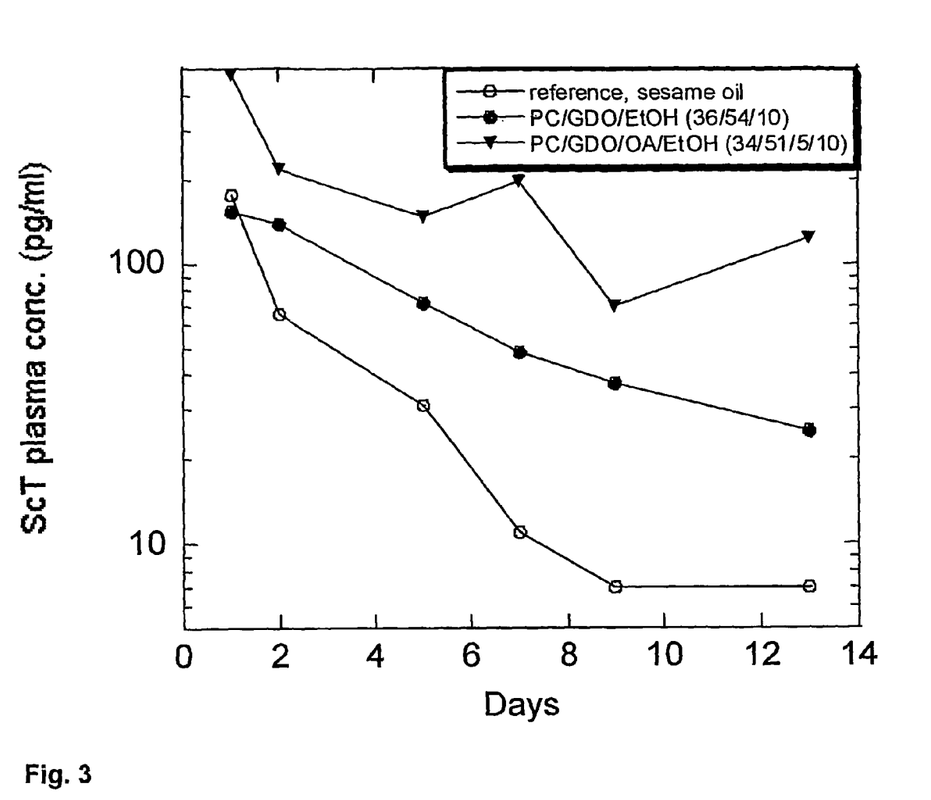
FIG. 3 Shows plasma concentrations of active agent in rats after subcutaneous administration of two depot formulations. A depot based on sesame oil was used as reference.

FIG. 3 shows the results. A pure triglyceride vehicle based on sesame oil was selected as a lipid reference system.

The formulation containing OA displays a slower release of sCT and an improved bioavailability over the 14 days period over which the plasma concentration was followed. This is consistent with an improved stability of the peptide drug.

The invention claimed is:

1. A composition comprising:
   at least one cationic peptide active agent having an isoelectric point of above 7.0,
   at least one neutral structure forming amphiphile comprising a diacyl lipid
   and a phospholipid in proportions 5:95 to 95:5 by weight,
   1 to 10% of at least one anionic structure forming amphiphile
   and 0.5 to 50 wt. % of an oxygen containing biotolerable organic solvent,
   wherein the non-polar groups of the structure forming amphiphiles are selected from $C_6$-$C_{32}$ alkyl and alkenyl groups, and wherein said composition forms a non-lamellar phase structure on exposure to body fluids.

2. A composition as claimed in claim 1 wherein said non-lamellar phase is a cubic, hexagonal phase or $L_3$ phase.

3. A composition as claimed in claim 1 wherein said cationic peptide is a peptide hormone.

4. A composition as claimed in claim 1 wherein said cationic peptide is selected from the group consisting of desmopressin, octreotide, salmon calcitonin and human calcitonin.

5. A composition as claimed in claim 1 wherein the oral bioavailability is at least 1% when measured as blood plasma concentration of active agent relative to intravenous administration in slaine solution.

6. A composition as claimed in claim 1 further comprising a peptidase inhibitor.

7. A composition as claimed in claim 1 wherein said neutral structure forming amphiphile comprises at least one of glyceryl dioleate (GDO), dioleyl phosphatidyl ethanolamine (DOPE), dioleyl phosphatidylcholine (DOPC), lyso-oleyl phosphatidylcholine (LOPC) and mixtures thereof.

8. A composition as claimed in claim 1 wherein said anionic structure forming amphiphile comprises at least one fatty acid.

9. A composition as claimed in claim 8 wherein said fatty acid is at least one of caproic, caprylic, capric, lauric, myristic, palmitic, phytanic, palmitolic, stearic, oleic, elaidic, linoleic, linolenic, arachidonic, behenic or lignoceric acids, their salts or mixtures thereof.

10. A composition as claimed in claim 1 wherein said anionic structure forming amphiphile is present in a quantity sufficient to increase the half-life of said peptide active agent in a solution of carboxypeptidase C by at least 50% relative to the half-life of an equivalent composition not including said anionic structure forming amphiphile.

11. A composition as claimed in claim 1 further comprising a fragmentation agent.

12. A pharmaceutical formulation comprising a composition as claimed in claim 1 and at least one pharmaceutically tollerable carrier or excipient.

13. A composition as claimed in claim 1 which comprises or forms particles of said non-lamellar phase structure.

14. A composition as claimed in claim 13 wherein said particles are colloidal.

15. A composition as claimed in claim 1 wherein said composition comprises a diacyl glycerol.

16. A composition as claimed in claim 1 wherein said active agent is released over a period of at least 2 to 14 days.

17. A method for the formation of a composition as claimed in claim 1 comprising forming particles which generate non-lamellar phase on exposure to body fluids, said particles comprising
   at least one neutral structure forming amphiphile comprising a diacyl lipid and a phospholipid in proportions 5:95 to 95:5 by weight,
   1 to 10 wt. % of at least one anionic structure forming amphiphile or salt thereof and
   0.5 to 50 wt. % of an oxygen containing organic solvent and subsequently contacting said particles with a solution of cationic peptide active agent.

18. A method for administering a cationic peptide to a patient comprising injection of a composition as claimed in claim 1 wherein in use said composition subsequently forms a non-lamellar "depot" in vivo, upon contact with a body fluid.

19. A method for protecting a peptide active agent from enzymic degredation in vivo said method comprising formulating said active agent as a composition as claimed in claim 1.

* * * * *